(12) United States Patent
Van Tol et al.

(10) Patent No.: US 11,123,096 B2
(45) Date of Patent: *Sep. 21, 2021

(54) ULTRASONIC SURGICAL DEVICE AND METHOD FOR DETECTION OF ATTACHMENT OF ULTRASONIC PROBE

(71) Applicant: Covidien LP, Mansfield, MA (US)

(72) Inventors: David J. Van Tol, Boulder, CO (US); Keith W. Malang, Longmont, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/840,523

(22) Filed: Apr. 6, 2020

(65) Prior Publication Data

US 2020/0229842 A1 Jul. 23, 2020

Related U.S. Application Data

(63) Continuation of application No. 14/739,011, filed on Jun. 15, 2015, now Pat. No. 10,610,253.

(51) Int. Cl.
*A61B 17/32* (2006.01)
*A61B 90/00* (2016.01)
(Continued)

(52) U.S. Cl.
CPC .............. *A61B 17/320092* (2013.01); *A61B 2017/0003* (2013.01); *A61B 2017/00017* (2013.01);
(Continued)

(58) Field of Classification Search
CPC .... A61B 17/320092; A61B 2090/0808; A61B 2090/0812; A61B 2017/320094;
(Continued)

(56) References Cited

U.S. PATENT DOCUMENTS 6,662,127 B2   12/2003   Wiener et al.
6,678,621 B2   1/2004    Wiener et al.
(Continued)

OTHER PUBLICATIONS

European Search Report in corresponding EP Application No. 16 17 4431, dated Oct. 12, 2016, 6 pages.
(Continued)

*Primary Examiner* — Ly D Pham
(74) *Attorney, Agent, or Firm* — Carter, DeLuca & Farrell LLP

(57) ABSTRACT

An ultrasonic surgical device includes a power source configured to generate power, an ultrasonic transducer electrically coupled to the power source and generating ultrasonic motion in response to the generated power, a sensor sensing current of the generated power supplied to the ultrasonic transducer, an ultrasonic probe mechanically couplable to the ultrasonic transducer, and a controller that receive a sensed current from the sensor, performs a frequency response analysis based on the sensed current, calculates a first resonant frequency and a first anti-resonant frequency of the transducer prior to coupling the ultrasonic probe based on the frequency response analysis, calculates a second resonant and second anti-resonant frequencies of the transducer based on the frequency response analysis prior to determining coupling to the ultrasonic transducer, and determines whether the ultrasonic probe is mechanically coupled to the ultrasonic transducer based on the first and second resonant and anti-resonant frequencies.

20 Claims, 8 Drawing Sheets

(51) Int. Cl.
*A61B 17/00* (2006.01)
*A61B 18/00* (2006.01)
*A61B 18/12* (2006.01)
*A61N 7/00* (2006.01)

(52) U.S. Cl.
CPC ............... *A61B 2017/00477* (2013.01); *A61B 2017/320094* (2017.08); *A61B 2018/00607* (2013.01); *A61B 2090/0808* (2016.02); *A61B 2090/0812* (2016.02); *A61B 2560/0276* (2013.01)

(58) Field of Classification Search
CPC .. A61B 2017/00017; A61B 2017/0003; A61B 2017/00477; A61B 2018/00607; A61B 2560/0276
USPC .......................................................... 702/65
See application file for complete search history.

(56) References Cited

U.S. PATENT DOCUMENTS

| | | |
|---|---|---|
| 7,546,781 B2 | 6/2009 | Takahashi |
| 2002/0049463 A1 | 4/2002 | Friedman et al. |
| 2002/0049552 A1 | 4/2002 | Wiener et al. |
| 2007/0063618 A1 | 3/2007 | Bromfield |
| 2007/0087930 A1 | 4/2007 | Priya |
| 2008/0129146 A1 | 6/2008 | Puskas |
| 2011/0178542 A1 | 7/2011 | Smith |
| 2012/0310262 A1 | 12/2012 | Messerly |
| 2014/0306581 A1 | 10/2014 | Garland |
| 2015/0148830 A1 | 5/2015 | Stulen et al. |

OTHER PUBLICATIONS

European Examination Report dated Sep. 10, 2018 issued in corresponding EP Appln. No. 16 174 431.3.

ULTRASONIC SURGICAL DEVICE AND METHOD FOR DETECTION OF ATTACHMENT OF ULTRASONIC PROBE

CROSS-REFERENCE TO RELATED APPLICATIONS

This application is a continuation of U.S. patent application Ser. No. 14/739,011 filed Jun. 15, 2015. The disclosure of the foregoing application is hereby incorporated by reference in its entirety herein.

BACKGROUND

Technical Field

The present disclosure relates to an ultrasonic surgical device for verifying integrity of mechanical coupling between an ultrasonic probe and an ultrasonic transducer of the ultrasonic surgical device. More specifically, the present disclosure relates to an ultrasonic surgical device configured to detect attachment of an ultrasonic probe to an ultrasonic transducer.

Background of Related Art

Ultrasonic surgical devices have been demonstrated to provide hemostasis and efficient dissection of tissue with minimum lateral thermal damage and low smoke generation. Unlike electrosurgical devices, which require electrical current to flow through a patient, ultrasonic surgical devices operate by applying mechanical motion through an ultrasonic probe using an ultrasonic transducer that is driven at a resonant frequency. Thus, the ultrasonic surgical devices do not harm tissue due to overexposure of electrical current being passed through the tissue.

However, when the ultrasonic transducer is not mechanically coupled or attached to the ultrasonic probe, the ultrasonic transducer cannot deliver desired mechanical motion so as to obtain desired therapeutic effects. Alternatively, absence of the ultrasonic probe may render the ultrasonic device inoperable as the ultrasonic transducer would be incapable of generating sufficient mechanical motion at the resonant frequency. Thus, there is a need for determining and analyzing the presence or absence of the connection of the ultrasonic probe and the ultrasonic transducer as well as for notifying a clinician of the absence of the ultrasonic probe.

SUMMARY

The present disclosure provides ultrasonic surgical devices, which include an ultrasonic transducer and an ultrasonic probe and are configured to analyze integrity of a mechanical coupling of the ultrasonic probe to the ultrasonic transducer. The present disclosure also provides a method for analyzing the connection between the ultrasonic probe and the ultrasonic transducer.

The ultrasonic surgical device includes a power source configured to generate power, an ultrasonic transducer electrically coupled to the power source and configured to generate ultrasonic motion in response to the generated power, a sensor configured to sense current of the generated power supplied to the ultrasonic transducer, an ultrasonic probe configured to be mechanically couplable to the ultrasonic transducer, and a controller. The controller is configured to receive sensed current from the sensor, perform a frequency response analysis based on the sensed current, calculate a first resonant frequency and a first anti-resonant frequency of the transducer prior to coupling the ultrasonic probe based on the frequency response analysis, calculate a second resonant frequency and a second anti-resonant frequency of the transducer based on the frequency response analysis prior to determining whether the ultrasonic probe is coupled to the ultrasonic transducer, and determine whether the ultrasonic probe is mechanically coupled to the ultrasonic transducer based on the first and second resonant frequencies and the first and second anti-resonant frequencies.

In an aspect, the controller is further configured to calculate a first coupling coefficient based on the first resonant frequency and the first anti-resonance frequencies. The first coupling coefficient is calculated using a formula:

$$k_1^2 = 1 - \frac{f_{r1}^2}{f_{a1}^2},$$

where $k_1$ is the first coupling coefficient, $f_{r1}$ is the first resonant frequency, and $f_{a1}$ is the first anti-resonant frequency.

In another aspect, the controller is further configured to calculate a second coupling coefficient based on the second resonant frequency and the second anti-resonance frequencies. The second coupling coefficient is calculated using a formula:

$$k_2^2 = 1 - \frac{f_{r2}^2}{f_{a2}^2},$$

where $k_2$ is the second coupling coefficient, $f_{r2}$ is the second resonant frequency, and $f_{a2}$ is the second anti-resonant frequency.

In another aspect, the controller is further configured to determine whether the ultrasonic probe is mechanically coupled to the ultrasonic transducer based on the first and second coupling coefficients. The controller is further configured to determine whether the ultrasonic probe is mechanically coupled to the ultrasonic transducer based on a comparison of a difference between the first and second coupling coefficients with a predetermined threshold.

In another aspect, the sensed current has a maximum amplitude response at the first resonant frequency and a minimum amplitude response at the first anti-resonant frequency in response to the ultrasonic probe not being mechanically coupled to the ultrasonic transducer.

In yet another aspect, the sensed current has a maximum amplitude response at the second resonant frequency and a minimum amplitude response at the second anti-resonant frequency in response to the ultrasonic probe being mechanically coupled to the ultrasonic transducer.

The method for detecting a mechanical coupling between an ultrasonic probe and an ultrasonic transducer of an ultrasonic surgical device includes obtaining a first resonant frequency and a first anti-resonant frequency of the ultrasonic transducer without the ultrasonic probe being mechanically coupled to the ultrasonic transducer, detecting a second resonant frequency and a second anti-resonant frequency of the ultrasonic transducer prior to determining whether the ultrasonic probe is mechanically coupled to the ultrasonic transducer, calculating a first coupling coefficient based on the first resonant frequency and the first anti-resonant frequency, calculating a second coupling coefficient based the second resonant frequency and the second anti-resonant frequency, and determining whether the ultrasonic probe is mechanically coupled to the ultrasonic transducer based on the first and second coupling coefficients.

In an aspect, obtaining the first resonant frequency and the first anti-resonant frequency includes applying broadband alternating current (AC) signals to the ultrasonic transducer without the ultrasonic probe being mechanically coupled to the ultrasonic transducer, sensing current of the broadband AC signals supplied to the ultrasonic transducer, performing a frequency response analysis of the sensed current, and detecting the first resonant frequency and the first anti-resonant frequency based on the frequency response analysis. The sensed current has a maximum amplitude response at the first resonant frequency and a minimum amplitude response at the first anti-resonant frequency.

In another aspect, detecting a second resonant frequency and a second anti-resonant frequency includes applying broadband alternating current (AC) signals to the ultrasonic transducer prior to determining whether the ultrasonic probe is mechanically coupled to the ultrasonic transducer, sensing current of the broadband AC signals supplied to the ultrasonic transducer, performing a frequency response analysis of the sensed current, and detecting the second resonant frequency and the second anti-resonant frequency based on the frequency response analysis. The sensed current has a maximum amplitude response at the second resonant frequency and a minimum amplitude response at the second anti-resonant frequency.

In another aspect, the first coupling coefficient is calculated using a formula:

$$k_1^2 = 1 - \frac{f_{r1}^2}{f_{a1}^2},$$

wherein $k_1$ is the first coupling coefficient, $f_{r2}$ is the first resonant frequency, and $f_{a2}$ is the first anti-resonant frequency.

In another aspect, the second coupling coefficient is calculated using a formula:

$$k_2^2 = 1 - \frac{f_{r2}^2}{f_{a2}^2},$$

where $k_2$ is the second coupling coefficient, $f_{r2}$ is the second resonant frequency, and $f_{a2}$ is the second anti-resonant frequency.

In yet another aspect, determining whether the ultrasonic probe is mechanically coupled to the ultrasonic transducer further includes comparing a difference between the first and second coupling coefficients with a predetermined threshold.

In an aspect, the method further includes displaying a message in response to the determination of whether the ultrasonic probe is mechanically coupled to the ultrasonic transducer.

In another aspect, the method further includes generating an optical or audible signal in response to the determination of whether the ultrasonic probe is mechanically coupled to the ultrasonic transducer.

BRIEF DESCRIPTION OF THE DRAWINGS

The present disclosure may be understood by reference to the accompanying drawings, when considered in conjunction with the subsequent, detailed description, in which.

DETAILED DESCRIPTION

Generally, the present disclosure provides an ultrasonic surgical device for detecting a defect in a connection between an ultrasonic transducer and an ultrasonic probe of an ultrasonic surgical device. The ultrasonic transducer is configured to generate ultrasonic mechanical motion at its resonant frequency. The ultrasonic surgical device also includes a processor that is programmed to detect a mechanical coupling between the ultrasonic transducer and the ultrasonic probe based on the changes in the resonant frequency of the ultrasonic transducer.

A pulse-width modulation (PWM) amplitude control is employed to regulate the mechanical motion of the ultrasonic probe and to provide different levels of power for treating tissue. Further, a proportional-integral (PI) controller is included to obtain a rapid transient response to changes in load and to maintain stable surgical operations.

The ultrasonic surgical device also includes two control loops, which may be embodied in hardware and/or software executed by the processor, to control the ultrasonic mechanical motion of the ultrasonic transducer, which is energized by a DC power source. The first loop is an amplitude control loop configured to regulate the longitudinal mode displacement and includes a closed-loop feedback control. The second loop generates an AC signal from the DC power supplied to the ultrasonic transducer and automatically tracks the resonant frequency of the ultrasonic transducer. The second control loop includes a band-pass filter oscillator. By using the first and second control loops, the ultrasonic surgical device provides regulated ultrasonic mechanical motion at resonant frequency sufficient to treat tissue in accordance with embodiments of this disclosure.

Figure 1A:
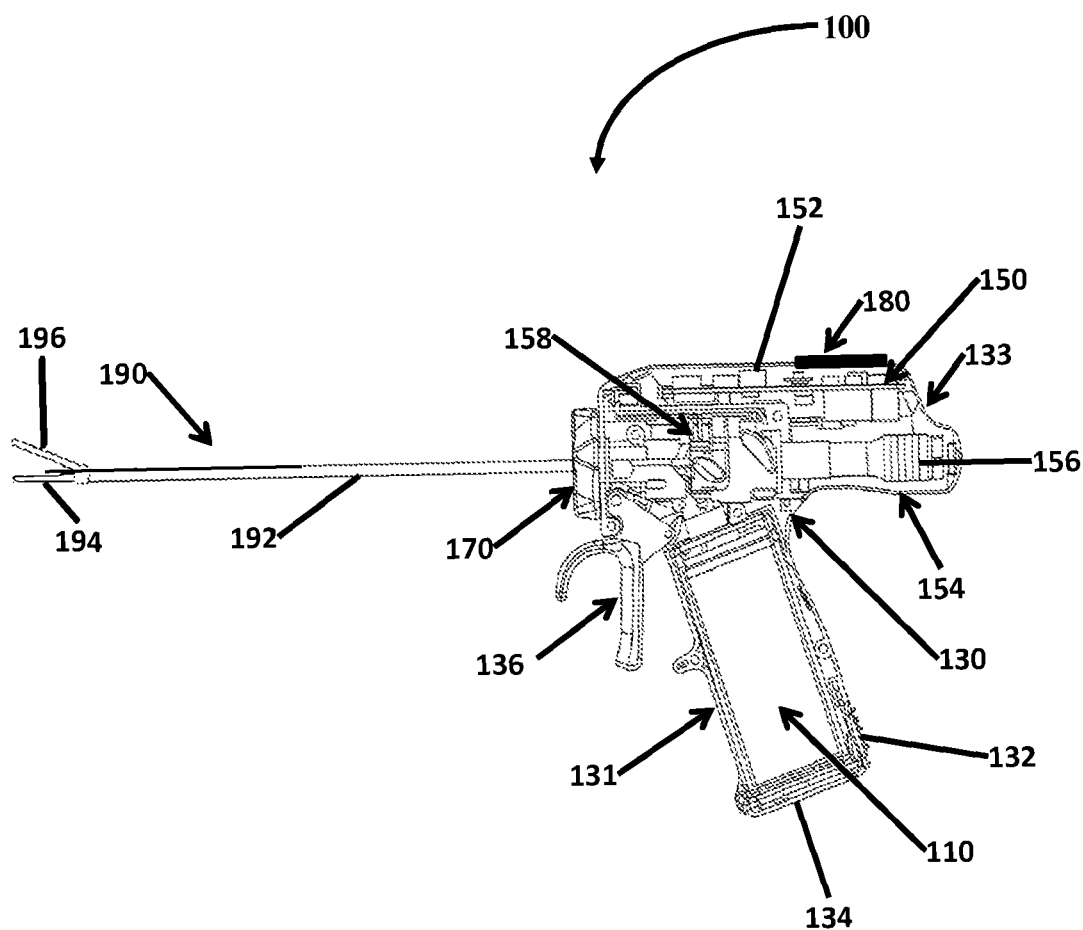
FIG. 1A is a side elevation view of an ultrasonic surgical device in accordance with embodiments of the present disclosure.
Figure 1B:
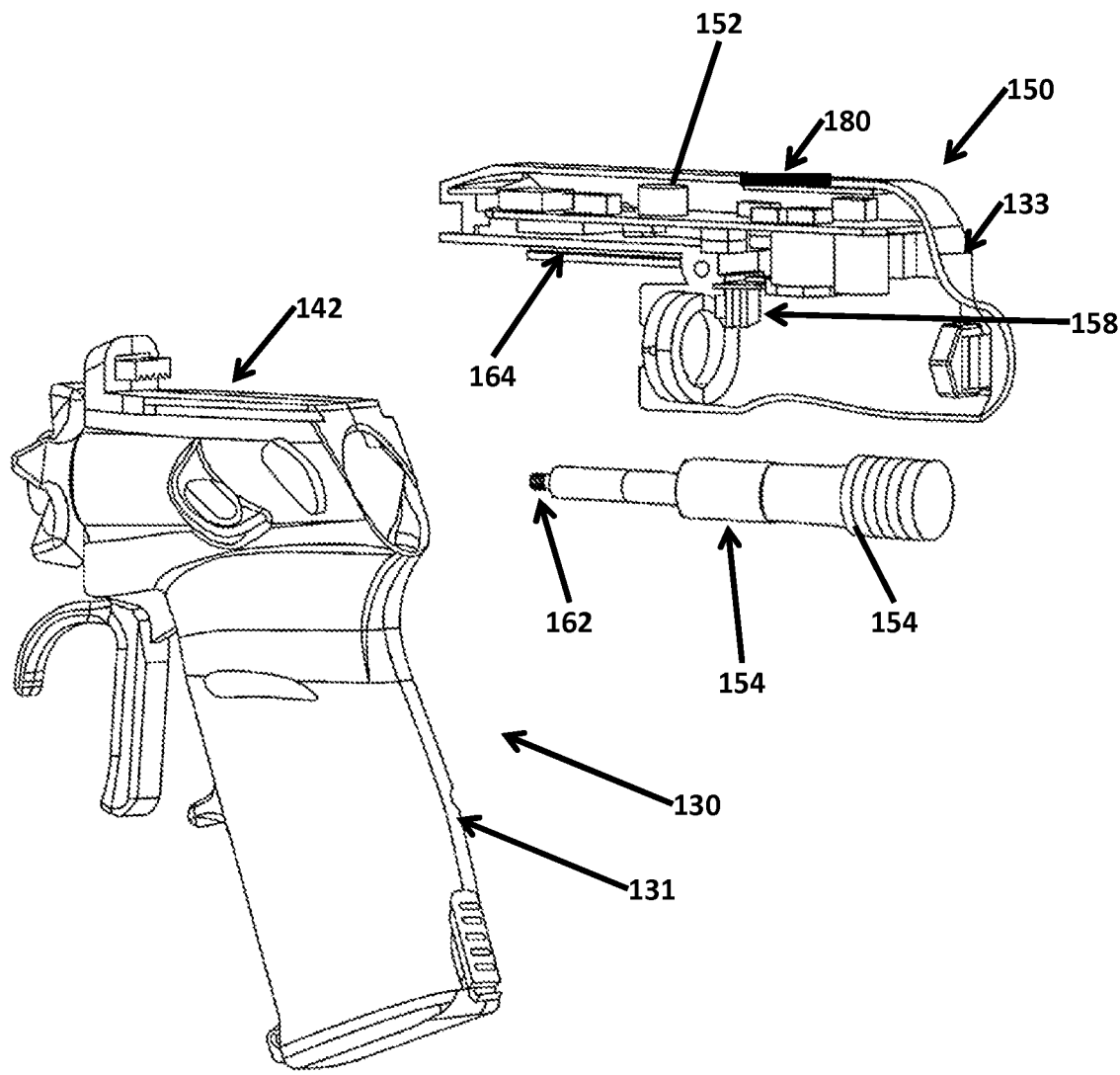
FIG. 1B is a perspective view of parts separated, which shows the left side of a handle, an ultrasonic transducer, and a right side of the handle of the ultrasonic surgical device of FIG. 1A in accordance with embodiments of the present disclosure.

With reference to FIGS. 1A-1B, an ultrasonic surgical device 100 for treating tissue is illustrated. The ultrasonic surgical device 100 includes a power source 110, a housing 130, an ultrasonic transducer 150, and an ultrasonic probe 190. The power source 110 provides DC power to the ultrasonic transducer 150. In an aspect, the power source 110 may be a battery that directly provides DC power. In a further aspect, the power source 110 may be insertable or integrated into the housing 130 so that the ultrasonic surgical device 100 may be portably carried without disturbances of any cable. In yet another aspect, the power source 110 may be rechargeable so that the power source 110 may be reusable.

In another aspect, the power source 110 may include a converter that is connected to an alternating current (AC) power source and converts the AC power to DC power. The AC power source may be of a relatively low frequency, such as about 60 hertz (Hz), while the ultrasonic surgical device 100 may operate at a higher frequency, such as 55.5 kilo hertz (kHz). Thus, the power source 110 may convert the low frequency AC power to DC power so that the DC power may then be inverted to AC power having a frequency suitable to cause the ultrasonic transducer 150 to generate ultrasonic mechanical motion.

With continued reference to FIGS. 1A and 1B, the housing 130 includes a handle portion 131 having a compartment 132, which houses the power source 110, and a power source door 134 that secures the power source 110 within the compartment 132. In an aspect, the power source door 134 may be configured to form a water-tight seal between the interior and the exterior of the compartment 132.

The housing 130 also includes a cover 133, which houses the ultrasonic transducer 150 and an output device 180. The ultrasonic transducer 150 includes a generator assembly 152 and a transducer assembly 154, having a transducer body 156 and a locking portion 162. The generator assembly 152 is electrically coupled to the transducer assembly 154 via a pair of contacts 158.

With reference to FIG. 1B, the ultrasonic transducer 150 is illustrated as being separate from the cover 133. When the ultrasonic transducer 150 is inserted into and assembled with the cover 133, the pair of contacts 158 is connected to the round groove of the ultrasonic transducer 150 so that the rotational movement of the transducer body 156 does not disrupt the connection between the transducer body 156 and the generator assembly 152. Thus, the transducer body 156 is capable of freely rotating within the housing 130.

The output device 180 outputs information about the ultrasonic surgical device 100 or a status of the mechanical coupling between the ultrasonic probe 190 and the ultrasonic transducer 150. The output device 180 may also display a warning that the ultrasonic probe 190 is not mechanically coupled to the ultrasonic transducer 150.

In another aspect, the output device 180 may be a speaker configured to output audible tones denoting no connection between the ultrasonic probe 190 and the ultrasonic transducer 150. In yet another aspect, the output device 180 may include one or more light emitting devices, configured to emit lights of various duration, pulses, and colors indicating the status of the mechanical coupling between the ultrasonic probe 190 and the ultrasonic transducer 150.

The handle portion 131 further includes a trigger 136. When the trigger 136 is actuated, the power source 110 provides energy to the ultrasonic transducer 150 so that the ultrasonic transducer 150 is powered to generate ultrasonic mechanical motion of the ultrasonic probe 190. As the trigger 136 is released, the power supply to the ultrasonic transducer 150 is terminated.

The generator assembly 152 receives the DC power from the power source 110 and generates AC signals having an ultrasonic frequency. The generator assembly 152 may be capable of generating signals having a frequency based on a desired mode of operation, which may be different from the resonant frequency of the ultrasonic transducer 150.

In an aspect, the generator assembly 152 may generate AC signals having a relatively wide range of frequencies (e.g., broadband signals) or a relatively small range of frequencies (e.g., narrowband signals). The broadband AC signals may be used to detect a resonant frequency and an anti-resonant frequency of the ultrasonic transducer 150. Presence or absence of the connection between the ultrasonic probe 190 and the ultrasonic transducer 150 may be analyzed based on the resonant and anti-resonant frequencies as described in further detail below.

The transducer body 156 of the transducer assembly 154 receives the AC signal generated by the generator assembly 152 and generates ultrasonic mechanical motion within the ultrasonic probe 190 based on the amplitude and the frequency of the generated AC signal. The transducer body 156 includes a piezoelectric material, which converts the generated AC signal into ultrasonic mechanical motion. The transducer body 156 may be based on an electrical oscillator model having an inductor and a capacitor, which oscillates between charging and discharging electrical energy. This oscillation model for the transducer body 156 is described further in detail below with respect to FIG. 4.

The ultrasonic surgical device 100 also includes a spindle 170, which is coupled to the ultrasonic probe 190 and allows for rotation of the ultrasonic probe 190 about its longitudinal axis. The ultrasonic probe 190 is attached to the housing and is mechanically coupled to the ultrasonic transducer 150 via the locking portion 162 such that as the spindle 170 is rotated about the longitudinal axis defined by the ultrasonic probe 190, the ultrasonic probe 190 and the ultrasonic transducer 150 are also rotated correspondingly without affecting the connection between the ultrasonic transducer 150 and the ultrasonic probe 190. Additionally, as the spindle 170 is rotated, the ultrasonic transducer 150 may be also rotated along with the ultrasonic probe 190.

FIG. 1B illustrates the ultrasonic transducer 150 separated from the handle portion 131 of the housing 130 of FIG. 1A. The ultrasonic transducer 150 includes a slidable first connector 164 and the handle portion 131 of the housing 130 includes a second connector 142 configured and dimensioned to engage the slidable first connector 164 allowing for selective engagement of the ultrasonic transducer 150 with the handle portion 131.

The locking portion 162 physically and/or mechanically locks the ultrasonic probe 190 to the ultrasonic transducer 150. The locking portion 162 maintains physical contact between the ultrasonic probe 190 and the transducer body 156 as the ultrasonic probe 190 is rotated. The locking portion 162 conveys the ultrasonic mechanical motion from the transducer body 156 to the ultrasonic probe 190 without losing the connection. In an aspect, the locking portion 162 may be a male connector and the ultrasonic probe 190 may include a counterpart female connector.

The ultrasonic probe 190 may include an end effector suitable for sealing tissue. The ultrasonic probe 190 includes a waveguide 192, a blade 194 extending from the waveguide 192, and a jaw member 196. The ultrasonic probe 190 is mechanically coupled to the transducer body 156 via the locking portion 162.

The jaw member 196 may be formed as a pivoting arm configured to grasp and/or clamp tissue between the jaw member 196 and the blade 194. When the jaw member 196 and the blade 194 grasp tissue and the blade 194 conveys the ultrasonic mechanical motion, temperature of the grasped tissue between the blade 194 and the jaw member 196 increases due to the ultrasonic mechanical motion. This motion in turn treats, e.g., cuts and/or seals, tissue.

In instances when the ultrasonic probe 190 is not attached to the ultrasonic transducer 150, the ultrasonic mechanical motion generated by the ultrasonic transducer 150 cannot be delivered to the ultrasonic probe 190. As a result, the ultrasonic surgical device 100 cannot be used to treat the tissue. The ultrasonic surgical device 100 according to the present disclosure is configured to determine whether or not the ultrasonic probe 190 is mechanically coupled to the ultrasonic transducer 150 to ensure operations of the ultrasonic probe 190.

Figure 2:
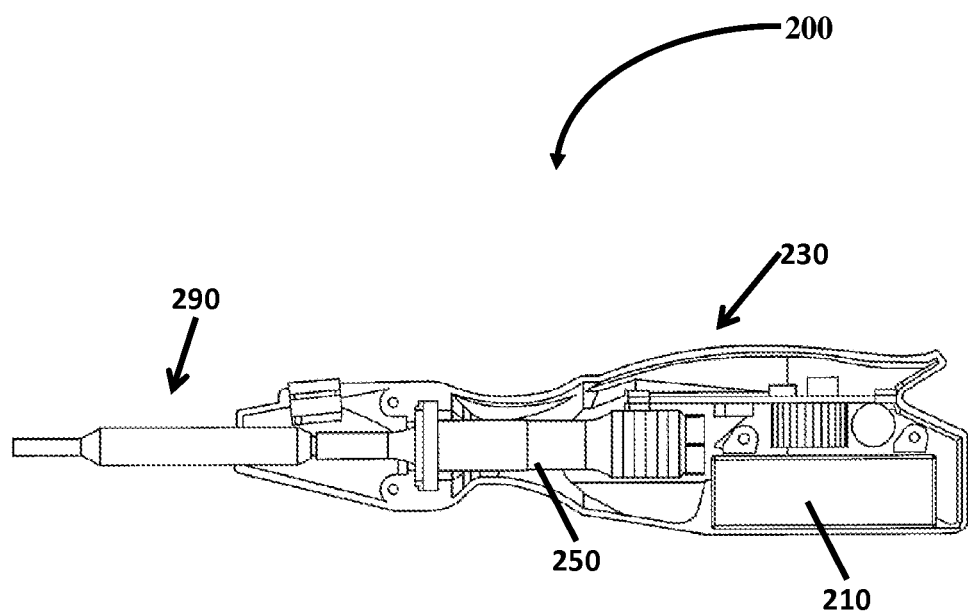
FIG. 2 is a side cross-sectional elevation view of an ultrasonic surgical pen in accordance with embodiments of the present disclosure.

FIG. 2 shows an ultrasonic surgical pen 200, which is another illustrative embodiment of the ultrasonic surgical device 100 of FIG. 1A. The ultrasonic surgical pen 200 includes a power source 210, the housing 230, the ultrasonic transducer 250, and the ultrasonic probe 290. The power source 210, the housing 230, and the ultrasonic transducer 250 of the ultrasonic surgical pen 200 are substantially similar to the power source 110, the housing 130, and the ultrasonic transducer 150 of the ultrasonic surgical device 100, respectively. The ultrasonic probe 290 may be an ultrasonic cauterizer. The shape and dimensions of the housing 230 of the ultrasonic surgical pen 200 also provide for a different ergonomic option than the ultrasonic surgical device 100.

Figure 3:
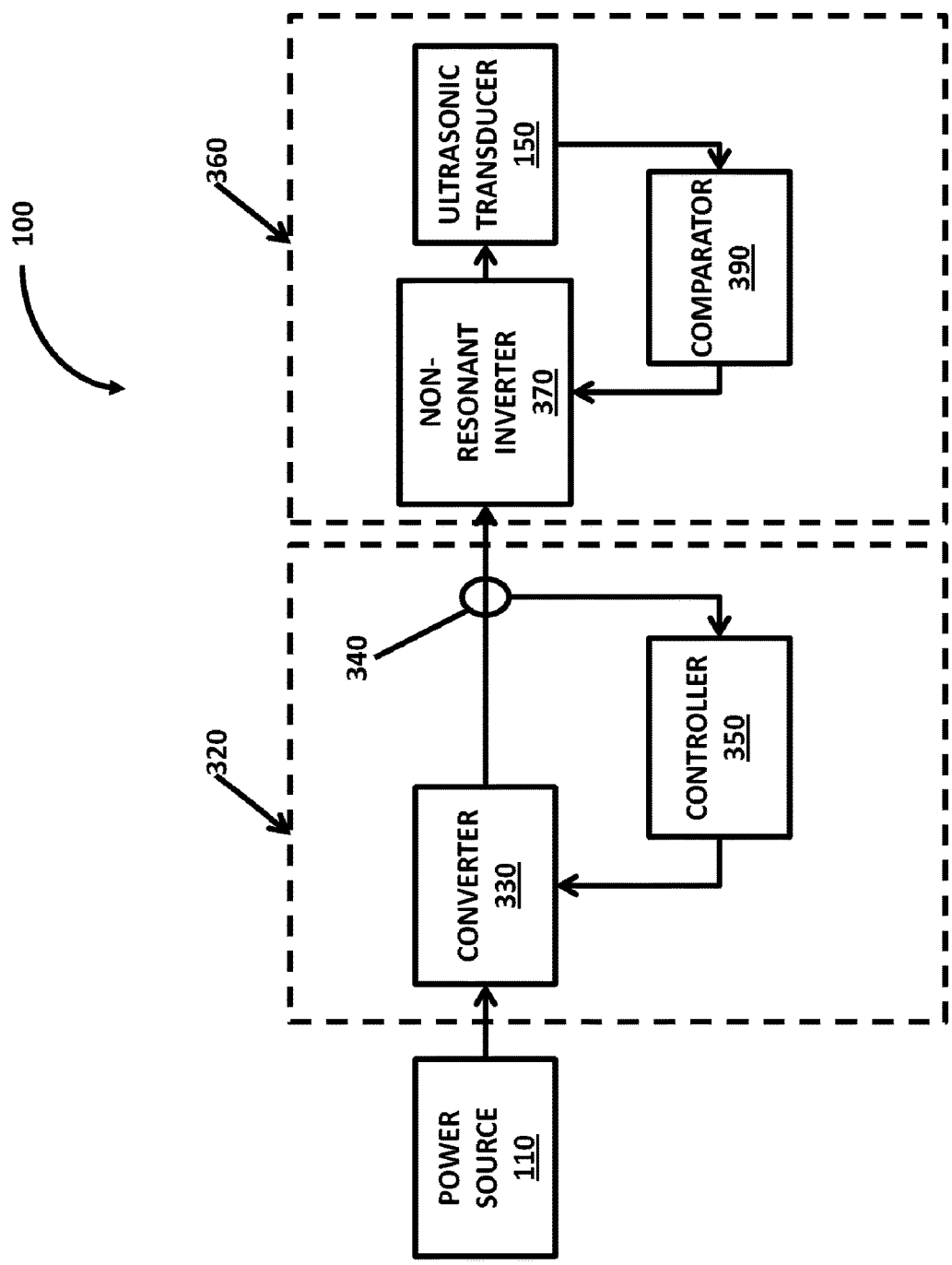
FIG. 3 is a block diagram of the ultrasonic surgical device of FIG. 1A in accordance with embodiments of the present disclosure.

FIG. 3 illustrates a block diagram of the ultrasonic surgical device 100 using a band-pass filter (BPF) oscillator architecture, which tracks the resonant frequency of the BPF regardless of process variations and environmental interferences. A pulse-width modulation (PWM) signal is used to regulate ultrasonic mechanical motion as described in further detail below.

The ultrasonic surgical device 100 includes the power source 110, an amplitude controller 320, and a resonance tracking controller 360. The amplitude controller 320 includes a converter 330, a sensor 340 and a controller 350. The resonance tracking controller 360 includes a non-resonant inverter 370, the ultrasonic transducer 150, and a comparator 390.

The power source 110 provides DC power to the amplitude controller 320, which controls amplitude of the output of the amplitude controller 320 so that ultrasonic surgical device 100 generates ultrasonic mechanical motion suitable for treating tissue. In an aspect, when the DC power is provided, the converter 330 amplifies the amplitude of the DC power. The converter 330 may be a buck converter or a step-down converter. The sensor 340 then senses current flowing to the resonance tracking controller 360. The controller 350 receives the sensed results from the sensor 340 and generates a digital pulse width modulated (PWM) control signal to control a duty cycle of the converter 330.

The resonant tracking controller 360 is configured to generate ultrasonic motion at a frequency substantially equal to the resonant frequency of the ultrasonic transducer 150. In an aspect, the non-resonant inverter 370 receives the amplified DC power from the converter 330 and inverts to AC power having a first frequency. The non-resonant inverter 370 is driven by output signals from the comparator 390. The comparator 390 adjusts the frequency of the AC power from an initial (e.g., first) frequency until the frequency is substantially equal to the resonant frequency of the ultrasonic transducer 150. The non-resonant inverter 370 may include any suitable electrical topology such as an H-bridge (e.g., full bridge), a half bridge, and the like.

In an aspect, the output signals from the comparator 390 may be digitally generated by the controller 350. The controller 350 may be a programmable gate array (PGA), field-programmable gate array (FPGA), application-specific integrated circuit (ASIC), complex programmable logic device (CPLD), or any other suitable logic device.

The controller 350 also generates PWM control signals to drive the converter 330 and resonant control signals for the non-resonant inverter 370. The controller 350 receives outputs from the comparator 390 and generates resonant signals for the non-resonant inverter 370 in response to the output of the comparator 390. The non-resonant inverter 370 then inverts the DC power to the AC signal, whose frequency is independent of the switching frequency of the non-resonant inverter 370, by tracking the resonant frequency of the ultrasonic transducer 150.

In an aspect, a transformer (not shown) may be electrically coupled between the non-resonant inverter 370 and the ultrasonic transducer 150 so that the transformer may increase or decrease the amplitude of the inverted AC power to a desired level.

The ultrasonic transducer 150 receives the AC power having a first frequency and generates ultrasonic mechanical motion. In a case when the frequency of the AC signals is different from the resonant frequency of the ultrasonic transducer 150, ultrasonic mechanical motion generated by the ultrasonic transducer 150 may not be optimal for intended purposes. The comparator 390 is configured to track the resonant frequency of the ultrasonic transducer 150 to cause the frequency of the AC signal to match the resonant frequency of the ultrasonic transducer 150 to provide for optimal operation of the ultrasonic transducer 150.

In an aspect, the resonance tracking controller 360 may include a resonant inverter (not shown) connected to the ultrasonic transducer 150 without the non-resonant inverter 370 and the comparator 390. The resonant inverter may be configured to invert the amplified DC signals and generate AC signal having a frequency substantially equal to the resonant frequency of the ultrasonic transducer 150.

In an aspect, the resonant tracking controller 360 may be used to detect a resonant frequency of the ultrasonic transducer 150. The sensor 340 is configured to sense voltage and current of the broadband AC signals applied to the ultrasonic transducer 150 and transmit the sensor signals to the controller 350. The controller 350 digitally processes the sensor signals and monitors the voltage and current values. Further, the controller 350 performs frequency response analysis (e.g., Fourier transformation, digital Fourier transformation, or other frequency related analysis) to identify amplitude response with respect to frequencies of the current. The resonant frequency of the ultrasonic transducer 150 may be a frequency at which the amplitude response of the current is the maximum and the anti-resonant frequency of the ultrasonic transducer 150 may be a frequency at which the amplitude response of the current is the minimum.

Figure 4:
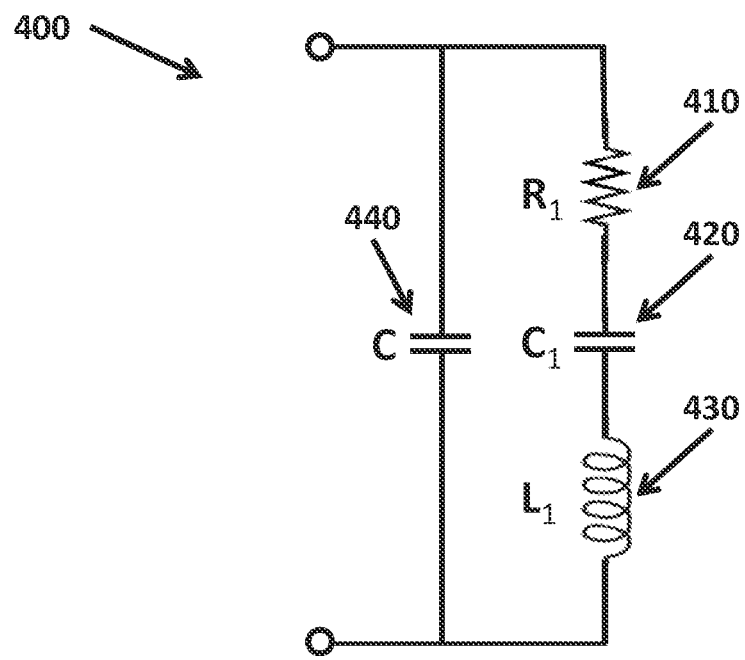
FIG. 4 is a circuit diagram illustrating a circuit model of an ultrasonic transducer or an ultrasonic transducer connected to the probe of the ultrasonic surgical device of FIG. 1A in accordance with embodiments of the present disclosure.

FIG. 4 shows electrical circuit models 400 and 450 of the ultrasonic transducer 150 of FIG. 1A in accordance with embodiments of the present disclosure. The electrical circuit model 400 or 450 model resonant or anti-resonant behavior of the ultrasonic transducer 150. The electrical circuit model 400 is a series resistor-inductor-capacitor (RLC) circuit including a resistor 410, a capacitor 420, and an inductor 430, which is connected in parallel with another capacity 440.

The resonant frequency $f_r$ of the circuit 400 is calculated using formula (I) below:

$$f_r = \frac{1}{2\pi\sqrt{L_1 \cdot C_1}}, \qquad (I)$$

where $L_1$ is the inductance of the inductor 430 and $C_1$ is the capacitance of the capacitor 420. Based on the circuit 400, the inductance and the capacitance of the ultrasonic transducer 150 determines the resonant frequency of the ultrasonic transducer 150.

The ultrasonic transducer 150 converts electrical energy into mechanical motion fully at the resonant frequency of the ultrasonic transducer 150. In other words, when the ultrasonic transducer 150 is operated at a frequency different from the resonant frequency, the ultrasonic transducer 150 does not operate optimally. Further, when the ultrasonic probe 190 is not mechanically coupled to the ultrasonic transducer 150, the ultrasonic probe 190 cannot deliver the ultrasonic motion to tissue for intended therapeutic purposes and the ultrasonic transducer 150 may maintain its resonant frequency and anti-resonant frequency.

In an aspect, the resonant frequency of the ultrasonic transducer 150 or the ultrasonic probe 190 may be obtained by testing and/or during manufacturing. In another aspect, the resonant frequencies may be measured and calculated or identified by the controller 350 of the ultrasonic surgical device 100. Determination of the resonant frequency may be accomplished using the comparator 390 with the non-resonant inverter 370, which can track the resonant frequency. The non-resonant inverter 370 may apply AC signals at a single frequency to the ultrasonic transducer 150 for a predetermined time and the comparator 390 may then track the frequency of the electrical energy until the resonant frequency is identified. The resonant frequency of the ultrasonic probe 190 may also be identified or measured using other techniques known in the related art.

In another aspect, when a broadband frequency AC signal is provided to the ultrasonic transducer 150, the controller 350 performs frequency response analysis and identifies the resonant frequency at which the frequency response is the maximum and the anti-resonant frequency at which the frequency response is the minimum.

When a voltage source is connected to the circuit 400, due to the potential difference, a current flows through the circuit 400. Then, the anti-resonant frequency $f_a$ of the 400 is calculated by:

$$f_a = \frac{1}{2\pi\sqrt{L_1 \cdot \left(\frac{C_1 \cdot C}{C_1 + C}\right)}}. \qquad (II)$$

This frequency $f_a$ is an anti-resonant frequency because the frequency response is the minimum at the anti-resonant frequency $f_a$, when the electrical impedance of the ultrasonic transducer 150 is the maximum.

Figure 5:
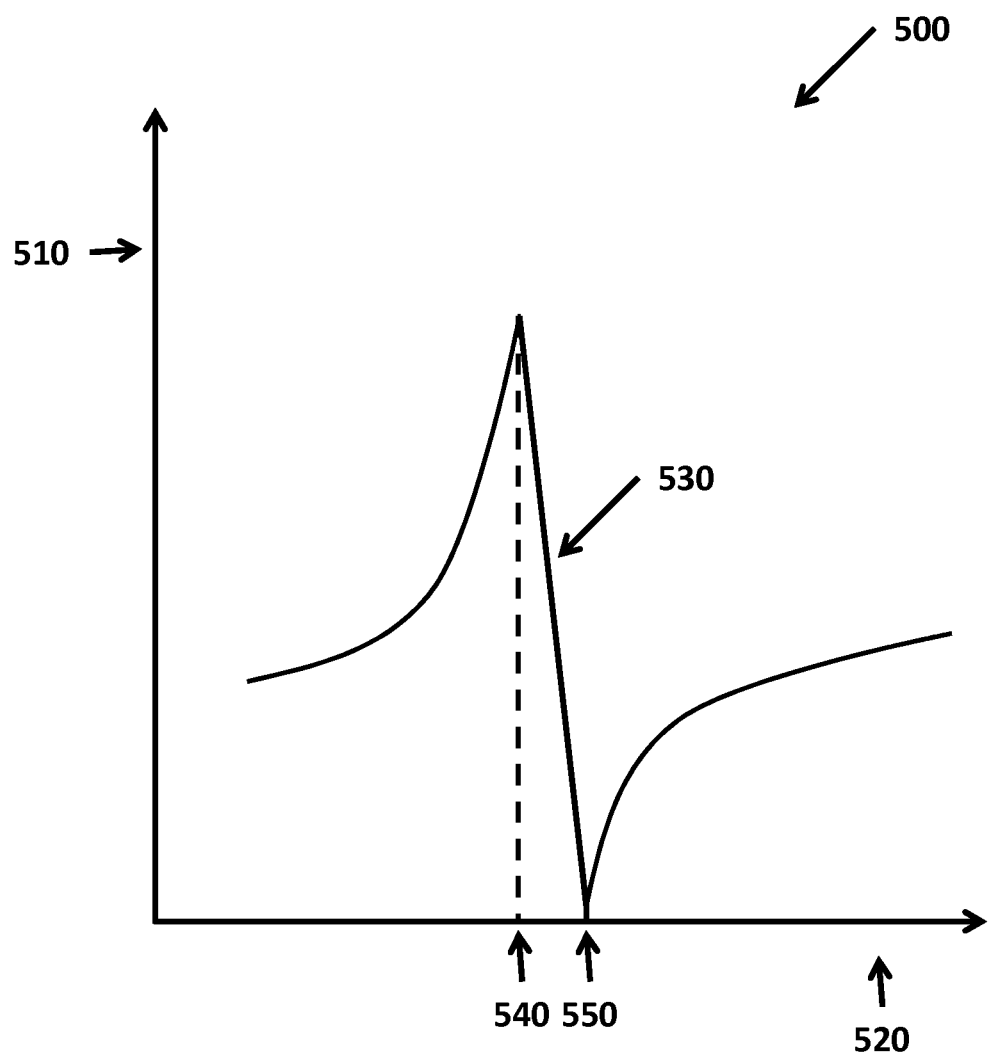
FIG. 5 is a graphical illustration of frequency responses of current flowing through an ultrasonic transducer in accordance with embodiments of the present disclosure.

FIG. 5 shows a frequency response graph 500 illustrating amplitude responses of current in frequency domain, which flows through the ultrasonic surgical device 100 in accordance with embodiments of the present disclosure. FIG. 5 also illustrates frequency responses at the resonant frequency $f_r$ and the anti-resonant frequency $f_a$. The vertical axis 510 of the frequency response graph 500 represents amplitudes of current passing through an ultrasonic transducer 150 of the ultrasonic surgical device 100 and the horizontal axis 520 of the frequency response graph 500 represents frequencies of the current. When broadband AC signals are applied to the ultrasonic transducer 150, a frequency response curve 530 may be obtained by the controller 350 of the ultrasonic surgical device 100. As shown in the frequency response curve 530, the amplitude of the current has the maximum value at a first frequency 540 and the minimum value at a second frequency 550. The first frequency 540 corresponds to the resonant frequency $f_r$ of the ultrasonic transducer 150 and the second frequency 550 corresponds to the anti-resonant frequency $f_a$ of the ultrasonic transducer 150.

The ultrasonic transducer 150 by itself or a combined body of the ultrasonic transducer 150 and the ultrasonic probe 190 exhibit different resonant and the anti-resonance frequencies. Thus, presence or absence of the ultrasonic probe 190 can be detected based on the resonant and anti-resonance frequencies. This will be further described below with respect to FIG. 7.

Figure 6:
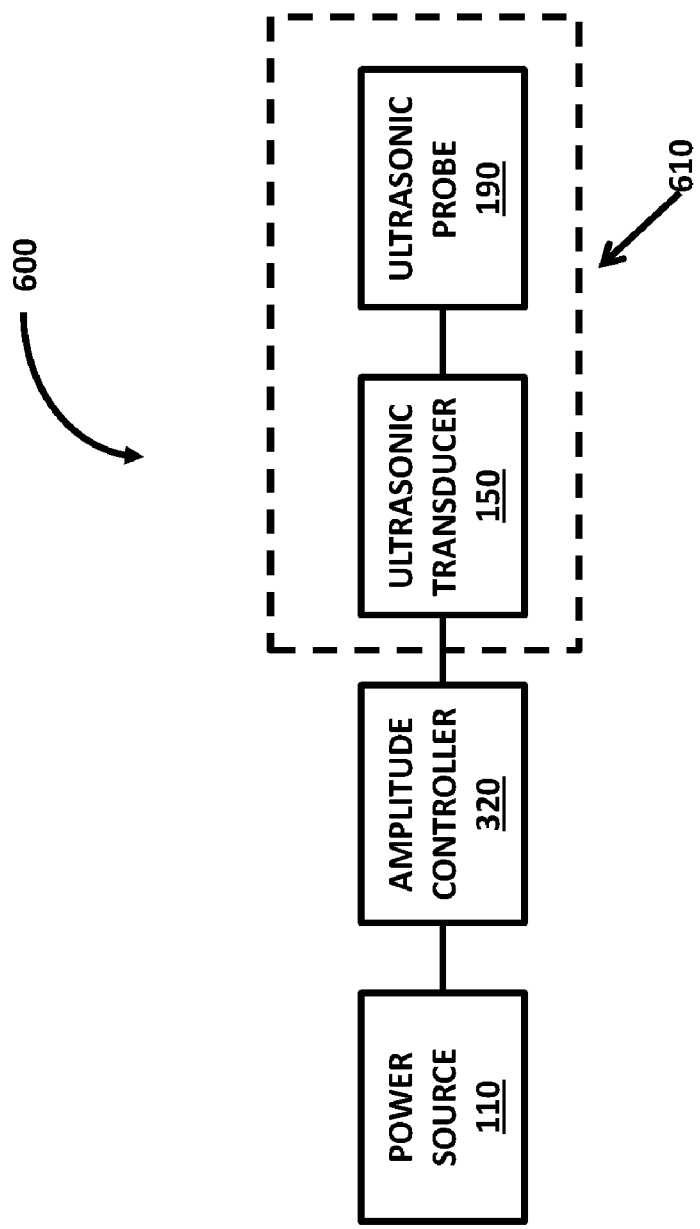
FIG. 6 is a block diagram illustrating coupling between the ultrasonic transducer and the ultrasonic probe of the ultrasonic surgical device of FIG. 1A in accordance with embodiments of the present disclosure.

FIG. 6 shows a block diagram 600 illustrating a connected state of the ultrasonic transducer 150 and the ultrasonic probe 190. The resonant and anti-resonant frequencies of the connected body 610 depend upon mechanical coupling between the ultrasonic probe 190 and the ultrasonic transducer 150. When the ultrasonic probe 190 is not mechanically coupled to the ultrasonic transducer 150, the connected body 610 may have resonant and anti-resonant frequencies similar to those of the ultrasonic transducer 150 not being coupled to the ultrasonic probe 190. When the ultrasonic probe 190 is mechanically coupled to the ultrasonic transducer 150, the connected body 610 will have resonant and/or anti-resonant frequencies different to those of the ultrasonic transducer 150.

The present disclosure utilizes coupling coefficients, which may be used to determine mechanical coupling between the ultrasonic transducer 150 and the ultrasonic probe 190. A first coupling coefficient $k_1$ is representative of the ultrasonic probe 190 being absent from the ultrasonic surgical device 100 or not being mechanically coupled to the ultrasonic transducer 150. The first coupling coefficient $k_1$ is calculated by:

$$k_1^2 = 1 - \frac{f_{r1}^2}{f_{a1}^2}, \qquad (III)$$

where $f_{r1}$ is the resonant frequency and $f_{a1}$ is the anti-resonant frequency of the ultrasonic transducer 150.

A second coupling coefficient $k_2$ is representative of the ultrasonic probe 190 being present in the ultrasonic surgical device 100 or being mechanically coupled to the ultrasonic transducer 150. In the same way, second coupling coefficient $k_2$ is calculated by:

$$k_2^2 = 1 - \frac{f_{r2}^2}{f_{a2}^2}, \qquad (IV)$$

where $f_{r2}$ is the resonant frequency and $f_{a2}$ is the anti-resonant frequency of the combined body 610.

When the second coupling coefficient $k_2$ differs significantly from the first coupling coefficient $k_1$, the ultrasonic probe 190 is determined to be present in the ultrasonic surgical device 100 or mechanically coupled to the ultrasonic transducer 150. After it is determined that the ultrasonic probe 190 is mechanically coupled to the ultrasonic transducer 150, it may be further determined whether or not the ultrasonic probe 190 is properly mechanically coupled to the ultrasonic transducer 150. Details of this determination may be found in a commonly assigned U.S. patent application Ser. No. 15/161,451, now U.S. Pat. No. 10,342,568, entitled "Ultrasonic Surgical Device and Method For Detection of Attachment of Ultrasonic Probe," the entire contents of which are incorporated by reference herein. Conversely, when the second coupling coefficient $k_2$ is substantially the same as the first coupling coefficient $k_1$, the ultrasonic probe 190 is absent in the ultrasonic surgical device 100.

Figure 7:
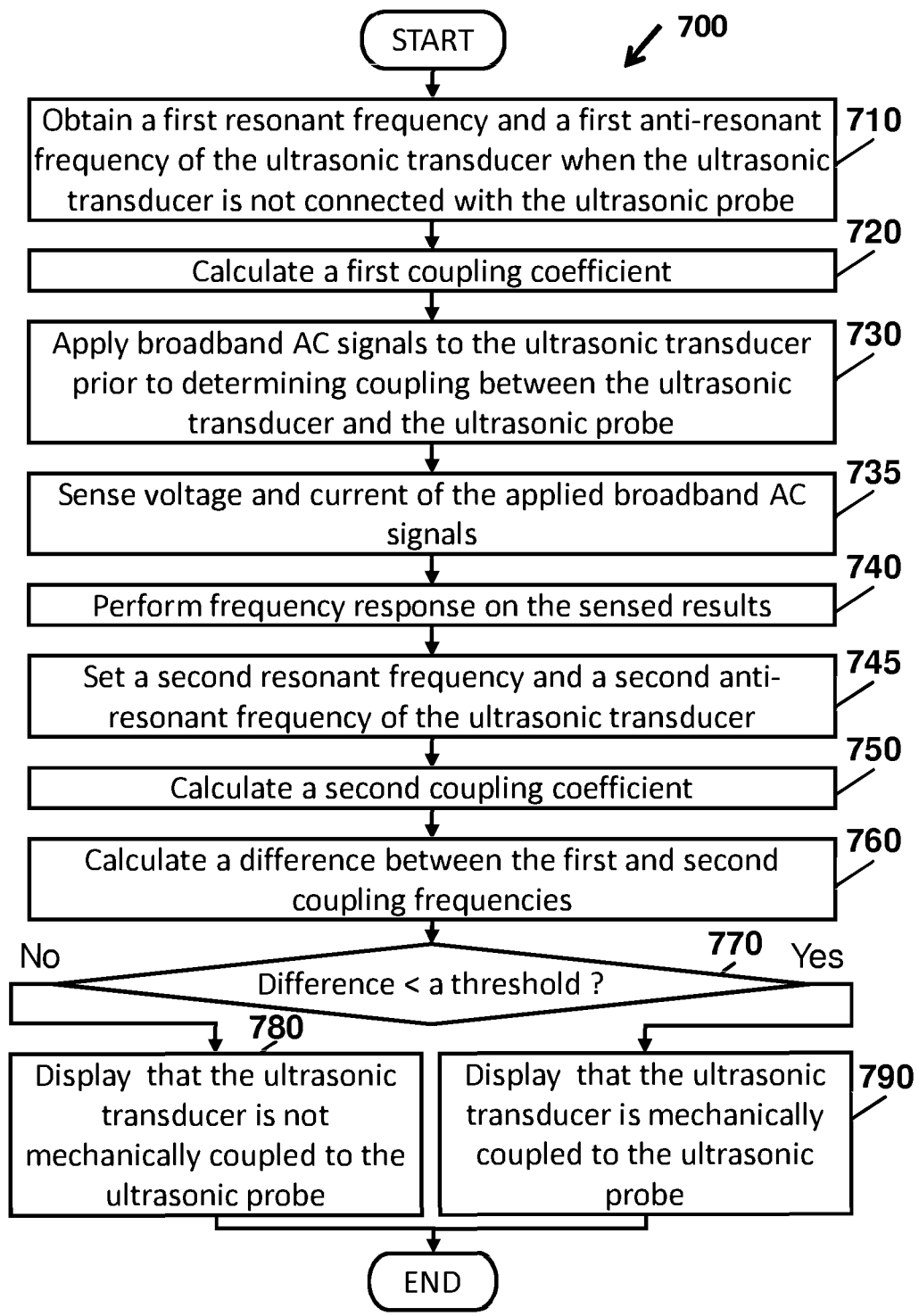
FIG. 7 is a flow chart of a method for analyzing the connection between the ultrasonic transducer and the ultrasonic probe in accordance with embodiments of the present disclosure.

FIG. 7 shows a method 700 for determining presence or absence of the ultrasonic probe 190 in the ultrasonic surgical device 100 in accordance with embodiments of the present disclosure. At step 710, a first resonant frequency and a first anti-resonant frequency of the ultrasonic transducer 150 are obtained, when the ultrasonic probe 190 is not coupled to the ultrasonic transducer 150. The first resonant and anti-resonant frequencies of the ultrasonic transducer 150 may be obtained in a manner described above.

In an aspect, first resonant and anti-resonant frequencies may be obtained from applying broadband AC signals to the ultrasonic transducer 150. A sensor of the ultrasonic surgical device 100 senses the broadband AC signals passing through the ultrasonic transducer 150 and transmits to a controller 350. The sensed results may be digitally sampled and then transmitted to the controller 350, which then performs frequency response analysis on the sensed results. The controller 350 may set a frequency, at which the amplitude response of the current is the maximum, as the first resonant frequency and set a frequency, at which the amplitude of the current is the minimum, as the first anti-resonant frequency.

In step 720, the controller 350 may calculate the first coupling coefficient $k_1$ using the formula (III) above. In step 730, before it is determined or when it is unknown whether or not the ultrasonic probe 190 is mechanically coupled to the ultrasonic transducer 150, the broadband AC signals are applied to the ultrasonic transducer 150. As noted above, the bandwidth of the broadband AC signals has a wide range of frequencies sufficient to include the first resonant and first anti-resonant frequencies.

In step 735, the sensor 340 senses the voltage and current of the applied broadband AC signals and transmits the measurements to the controller 350. As described above, the sensed results may be digitally sampled. The controller 350 performs frequency response analysis on the sensed results in step 740.

In step 745, the controller 350 calculates a second resonant frequency as a frequency at which the amplitude of the current is at its maximum based on the frequency response analysis and calculates a second anti-resonant frequency as a frequency at which the amplitude response of the current is at its the minimum.

In step 750, the controller 350 may calculate the second coupling coefficient $k_2$ using the formula (IV) above. The controller 350 also calculates a difference between the first and second coupling coefficients in step 760. The difference is compared with a predetermined threshold in step 770 to determine if there is a substantial difference between coupling coefficients, which is indicative of the ultrasonic probe 190 being attached to the ultrasonic transducer 150. When it is determined that the difference is less than the predetermined threshold, in step 780, a message is displayed to indicate that the ultrasonic probe 190 is absent in the ultrasonic surgical device 100 or is not mechanically coupled to the ultrasonic transducer 150.

When it is determined that the difference is greater than or equal to the predetermined threshold in step 770, in step 790, a message is displayed to indicate that the ultrasonic probe 190 is present in the ultrasonic surgical device 100 or is mechanically coupled to the ultrasonic transducer 150. By displaying a message in step 780 or 790, the method 700 for determining presence or absence of the ultrasonic probe 190 is ended.

In an aspect, when the message indicates that the ultrasonic probe 190 is absent in the ultrasonic surgical device 100 or is not mechanically coupled to the ultrasonic transducer 150 in step 780, a clinician using the ultrasonic surgical device 100 may connect the ultrasonic probe 190 with the ultrasonic transducer 150 so that the clinician can use the ultrasonic surgical device 100 to perform operations.

Since other modifications and changes may be made to fit particular operating requirements and environments, it is to be understood by one skilled in the art that the present disclosure is not limited to the illustrative examples described herein and may cover various other changes and modifications which do not depart from the spirit or scope of this disclosure.

What is claimed is:

1. An ultrasonic surgical device comprising:
an ultrasonic transducer configured to generate ultrasonic motion in response to current supplied from a power source;
an ultrasonic probe configured to be couplable to the ultrasonic transducer; and
a controller configured to:
perform a frequency response analysis based on the current supplied to the ultrasonic transducer;
calculate a first resonant frequency and a first anti-resonant frequency of the ultrasonic transducer based on the frequency response analysis prior to coupling the ultrasonic probe to the ultrasonic transducer;
calculate a second resonant frequency and a second anti-resonant frequency of the ultrasonic transducer based on the frequency response analysis after coupling the ultrasonic probe to the ultrasonic transducer; and
determine whether the ultrasonic probe is properly coupled to the ultrasonic transducer based on the first and second resonant frequencies and the first and second anti-resonant frequencies.

2. The ultrasonic surgical device according to claim 1, wherein the controller is configured to calculate a first coupling coefficient based on the first resonant frequency and the first anti-resonant frequency.

3. The ultrasonic surgical device according to claim 2, wherein the first coupling coefficient is calculated based on formula (I):

$$k_1^2 = 1 - \frac{f_{r1}^2}{f_{a1}^2}, \tag{I}$$

where $k_1$ is the first coupling coefficient, $f_{r1}$ is the first resonant frequency, and $f_{a1}$ is the first anti-resonant frequency.

4. The ultrasonic surgical device according to claim 3, wherein the controller is configured to calculate a second coupling coefficient based on the second resonant frequency and the second anti-resonant frequency.

5. The ultrasonic surgical device according to claim 4, wherein the second coupling coefficient is calculated based on formula (II):

$$k_2^2 = 1 - \frac{f_{r2}^2}{f_{a2}^2}, \tag{II}$$

where $k_2$ is the second coupling coefficient, $f_{r2}$ is the second resonant frequency, and $f_{a2}$ is the second anti-resonant frequency.

6. The ultrasonic surgical device according to claim 5, wherein the controller is configured to determine whether the ultrasonic probe is properly coupled to the ultrasonic transducer based on the first and second coupling coefficients.

7. The ultrasonic surgical device according to claim 6, wherein the controller is configured to determine whether the ultrasonic probe is properly coupled to the ultrasonic transducer based on a comparison of a difference between the first and second coupling coefficients with a predetermined threshold.

8. The ultrasonic surgical device according to claim 1, further comprising:
a sensor configured to sense current supplied to the ultrasonic transducer.

9. The ultrasonic surgical device according to claim 8, wherein the current has a maximum amplitude response at the first resonant frequency and a minimum amplitude response at the first anti-resonant frequency.

10. The ultrasonic surgical device according to claim 8, wherein the current has a maximum amplitude response at the second resonant frequency and a minimum amplitude response at the second anti-resonant frequency.

11. A method for detecting a proper coupling between an ultrasonic probe and an ultrasonic transducer of an ultrasonic surgical device, the method comprising:
performing a first frequency response analysis based on current supplied to an ultrasonic transducer prior to coupling an ultrasonic probe to the ultrasonic transducer;
calculating a first resonant frequency and a first anti-resonant frequency of the ultrasonic transducer based on the first frequency response analysis;
performing a second frequency response analysis based on current supplied to the ultrasonic transducer after coupling the ultrasonic probe to the ultrasonic transducer;
calculating a second resonant frequency and a second anti-resonant frequency of the ultrasonic transducer based on the second frequency response analysis; and
performing a determination whether the ultrasonic probe is properly coupled to the ultrasonic transducer based on the first and second resonant frequencies and the first and second anti-resonant frequencies.

12. The method according to claim 11, wherein the current is a broadband alternating current signal.

13. The method according to claim 11, wherein the current supplied to the ultrasonic transducer has a maximum amplitude response at the first resonant frequency and a minimum amplitude response at the first anti-resonant frequency.

14. The method according to claim 11, further comprising:
calculating a first coupling coefficient based on the first resonant frequency and the first anti-resonant frequency; and
wherein the first coupling coefficient is calculated based on formula (I):

$$k_1^2 = 1 - \frac{f_{r1}^2}{f_{a1}^2}, \tag{I}$$

wherein $k_1$ is the first coupling coefficient, $f_{r1}$ is the first resonant frequency, and $f_{a1}$ is the first anti-resonant frequency.

15. The method according to claim 14, wherein the current supplied to the ultrasonic transducer has a maximum amplitude response at the second resonant frequency and a minimum amplitude response at the second anti-resonant frequency.

16. The method according to claim 14, further comprising:
calculating a second coupling coefficient based the second resonant frequency and the second anti-resonant frequency; and
wherein the second coupling coefficient is calculated based on formula (II):

$$k_2^2 = 1 - \frac{f_{r2}^2}{f_{a2}^2}, \tag{II}$$

where $k_2$ is the first coupling coefficient, $f_{r2}$ is the second resonant frequency, and $f_{a2}$ is the second anti-resonant frequency.

17. The method according to claim 16, wherein the current supplied to the ultrasonic transducer has a maximum amplitude response at the second resonant frequency and a minimum amplitude response at the second anti-resonant frequency.

18. The method according to claim 16, wherein performing the determination of whether the ultrasonic probe is mechanically coupled to the ultrasonic transducer includes comparing a difference between the first and second coupling coefficients with a threshold.

19. The method according to claim 11, further comprising displaying a message in response to the determination of whether the ultrasonic probe is mechanically coupled to the ultrasonic transducer.

20. The method according to claim 11, further comprising generating an optical or audible signal in response to the determination of whether the ultrasonic probe is properly coupled to the ultrasonic transducer.

* * * * *